United States Patent
Nissilä et al.

(10) Patent No.: US 6,554,773 B1
(45) Date of Patent: Apr. 29, 2003

(54) METHOD AND ARRANGEMENT FOR BLOOD PRESSURE MEASUREMENT

(75) Inventors: Seppo Nissilä, Oulu (FI); Antti Ruha, Oulu (FI); Hannu Sorvoja, Oulu (FI); Mika Niemimäki, Oulu (FI); Mika Sorvisto, Ylivieska (FI)

(73) Assignee: Polar Electro Oy (FI)

( * ) Notice: Subject to any disclaimer, the term of this patent is extended or adjusted under 35 U.S.C. 154(b) by 0 days.

(21) Appl. No.: 09/508,355

(22) PCT Filed: Sep. 14, 1998

(86) PCT No.: PCT/FI98/00718
§ 371 (c)(1),
(2), (4) Date: Jun. 7, 2000

(87) PCT Pub. No.: WO99/13767
PCT Pub. Date: Mar. 25, 1999

(30) Foreign Application Priority Data
Sep. 12, 1997 (FI) .................................. 973678

(51) Int. Cl.⁷ .............................................. A61B 5/02
(52) U.S. Cl. .................... 600/485; 600/490; 600/494
(58) Field of Search ................................ 600/481, 485, 600/490, 493–496, 500

(56) References Cited

U.S. PATENT DOCUMENTS

| | | | |
|---|---|---|---|
| 4,117,835 A | 10/1978 | Williams | |
| 4,938,227 A | 7/1990 | Niwa et al. | |
| 5,000,187 A * | 3/1991 | Higuchi et al. | 600/494 |
| 5,033,471 A | 7/1991 | Yokoe et al. | |
| 5,144,956 A | 9/1992 | Souma | |
| 5,193,548 A * | 3/1993 | Miyawaki | 600/494 |
| 5,279,303 A | 1/1994 | Kawamura et al. | |
| 5,368,039 A * | 11/1994 | Moses | 600/494 |
| 5,427,109 A * | 6/1995 | Frankenreiter | 600/494 |
| 5,447,161 A | 9/1995 | Blazek et al. | |
| 5,590,649 A * | 1/1997 | Caro et al. | 600/500 X |
| 5,690,119 A * | 11/1997 | Rytky et al. | 128/903 X |
| 5,699,807 A * | 12/1997 | Motogi et al. | 600/494 |
| 5,906,581 A * | 5/1999 | Tsuda | 600/490 X |
| 6,283,922 B1 * | 9/2001 | Goto et al. | 600/494 |

FOREIGN PATENT DOCUMENTS

| | | | |
|---|---|---|---|
| DE | 26 05 528 A1 | | 8/1977 |
| DE | WO97/03606 | * | 2/1997 |
| EP | 0 651 969 A3 | | 5/1995 |
| WO | WO 97/03606 | | 2/1997 |

* cited by examiner

Primary Examiner—Robert L. Nasser
(74) Attorney, Agent, or Firm—Hoffmann & Baron, LLP

(57) ABSTRACT

A method and arrangement for blood pressure measurement are disclosed. In the method, a variable, compressive, acting pressure is applied to a compression, such as a person's extremity, by a pressure generator, and simultaneously, the effect of the variable acting pressure on the extremity is measured at a second point, the second point being farther from the heart than the compression point. The method determines diastolic and systolic pressure. The measured value of the variable acting pressure acting on the compression point is transferred to an interpreting unit, which also receives a pressure pulse generated by the heart. The pressure pulse is measured by a sensor at the second point for determining the effect of the variable acting pressure on the extremity. Further, diastolic pressure is determined int he interpreting unit based on the variable acting pressure, as the pressure when the interpreting unit detects a change in a trend of a characteristic of the pressure pulse indicative of magnitude.

52 Claims, 5 Drawing Sheets

METHOD AND ARRANGEMENT FOR BLOOD PRESSURE MEASUREMENT

FIELD OF THE INVENTION

The invention relates to a method for blood pressure measurement, in which method a variable compressive acting pressure is applied to a measuring point, such as a person's extremity or the like, at a compression point by a pressure generator, and at the same time the effect of the variable acting pressure on the artery is measured at a second point, the second point being located farther away from the heart, i.e. closer to the end point of peripheral circulation, than the compression point to which the acting pressure is applied, and in which method diastolic pressure is determined.

The invention also relates to a method for blood pressure measurement, in which method a variable compressive acting pressure is applied to a measuring point, such as a person's extremity or the like, at a compression point by a pressure generator, and at the same time the effect of the variable acting pressure on the artery is measured at a second point, the second point being located farther away from the heart, i.e. closer to the end point of peripheral circulation, than the compression point to which the acting pressure is applied, and in which method systolic pressure is determined.

The invention further relates to an arrangement for blood pressure measurement, comprising a pressure generator for applying a compressive acting pressure to a measuring point, such as a person's extremity or the like, the arrangement comprising an acting pressure measuring element, the arrangement further comprising an interpreting unit arranged to determine diastolic pressure, the arrangement comprising a sensor for simultaneous measurement of the effect of the variable acting pressure on an artery at a second point, said second point being farther away from the heart, i.e. closer to the end point of peripheral circulation, than the compression point to which the acting pressure is applied.

The invention also relates to an arrangement for blood pressure measurement, comprising a pressure generator for applying a compressive acting pressure to a measuring point, such as a person's extremity or the like, the arrangement comprising an acting pressure measuring element, the arrangement further comprising an interpreting unit arranged to determine systolic pressure, the arrangement comprising a sensor for simultaneous measurement of the effect of the variable acting pressure on an artery at a second point, said second point being farther away from the heart, i.e. closer to the end point of peripheral circulation, than the compression point to which the acting pressure is applied.

BACKGROUND OF THE INVENTION

The heart pumps and causes blood to flow in the blood vessels, arteries and veins. The pumping produces pressure in the blood, i.e. blood pressure. Blood pressure is particularly affected by heartbeat and the resistance provided by peripheral circulation. Psychic factors, medication, smoking and other factors, such as a person's state, i.e. whether a person is asleep or awake, are also important.

The terms systolic pressure, diastolic pressure and venous pressure, are used when discussing blood pressure.

Technically, from the point of view of measurement, systolic pressure refers to the pressure at which an artery becomes blocked, i.e. heartbeat stops. Physiologically, systolic pressure refers to the maximum pressure generated by a pumping cycle of the heart.

Technically, from the point of view of measurement, diastolic pressure refers to the pressure at which heartbeat is resumed when the pressure pressing the artery is reduced. Physiologically, diastolic pressure refers to the minimum venous pressure value between two pumping cycles of the heart.

Venous pressure refers to the average pressure in a vein. At a certain stage of venous pressure measurement, a systolic and diastolic point can also be detected.

Blood pressure measurement is divided into two main categories: invasive, i.e. measurement from inside the body, and non-invasive, i.e. measurement from the outside of the body. The drawback in the invasive method is naturally that the measurement is made from inside a person's body by the use of e.g. a catheter placed in an artery. The invasive method and the equipment solutions involved are unpleasant for a person, and the measurements involve much work and are cumbersome, since they require operating theatre conditions. A special drawback is the risk of infection and bleeding of the artery.

Currently two methods are known for non-invasive blood pressure measurement, i.e. measurement from outside of the body. These include the auscultatory measurement and the oscillometric measurement. The auscultatory method utilizes a stethoscope and an occluding cuff provided with a mercury manometer and a pressure pump, the cuff encircling a person's extremity, such as the arm. The auscultatory method is based on auscultation of sounds known as the Korotkoff sounds by the stethoscope. The Korotkoff sounds are created by blood flowing in a partially occluded artery. In the auscultatory method the pressure of the occluding cuff, i.e. the acting pressure, is first raised above the estimated systolic pressure, whereby blood flow in the extremity being measured, such as the arm, is occluded. The pressure of the occluding cuff is then allowed to decline gradually, while the stethoscope is placed over the artery for auscultation on the distal side with respect to the occluding cuff. Once the pressure has been lowered sufficiently, snapping Korotkoff sounds can be detected by the stethoscope, and the current pressure is interpreted as the systolic pressure. Once the pressure of the occluding cuff is allowed to decline further, Korotkoff sounds are no longer heard, which means that the current pressure is the diastolic pressure at which the occluding cuff no longer occludes the artery. The drawback of the auscultatory method is its inaccuracy and that it requires an intent and experienced user.

Publication DE-2605528 teaches an application of the auscultatory method which additionally utilizes an optic pulse sensor disposed on the finger for following the variations in the pressure pulse. If the pressure pulse measured by the optic pulse sensor is observed to vary, this indicates a change in blood pressure from the previous measurement, and requires a new measurement. However, said procedure does not allow improvement of the accuracy and reliability of a single measurement, only that said information indicates the need for a repeat measurement.

Furthermore, a manual method based on palpation is known, in which pressure is produced by an occluding cuff in the arm, and a finger is used to palpate the pressure pulse of the radial artery, i.e. heartbeat. However, said method is inaccurate and unreliable.

Another widely used non-invasive method is the oscillometric measurement, in which an occluding cuff and the same principle are used, i.e. the acting pressure is first raised high, i.e. over the estimated systolic pressure, and then slowly declined, during which a pressure sensor comprised by the cuff is used to follow or observe the pressure oscillation signal of the cuff. Thus the essential difference as compared with the auscultatory method is that in the oscillometric method an electronic monitoring unit comprised by the device is used to follow the pressure oscillation measured by the pressure sensor inside the cuff instead of auscultation of an artery. As cuff pressure falls, the amplitude of the pressure oscillation in the cuff, i.e. the AC signal of the cuff pressure, increases to a certain pressure as the pressure is lowered, whereupon the oscillation decreases. When the pressure falls, oscillation, i.e. an AC-form pressure oscillation signal, or amplitude variation, is detectable in the cuff pressure. The amplitude of the pressure oscillation signal oscillation measured by the pressure sensor from the cuff reaches its maximum at a pressure known as mean arterial pressure. Systolic pressure can be measured relatively well by the oscillometric method, but diastolic pressure has to be calculated indirectly since the pressure oscillation signal oscillation measured by the cuff pressure sensor is still present at diastolic pressure, and hence indirect determination is used, in which the value of the diastolic pressure is the mean arterial pressure minus half of the difference between systolic and mean arterial pressure. A weakness of the oscillometric method is its inaccuracy and the resulting unreliability. Oscillometric devices and methods are technically simple, but this in turn results in the inability to monitor and observe the measurement and its reliability. The accuracy and reliability of oscillometric measurement have been improved by different signal processing methods by identifying different characteristics of the AC signal of the pressure pulse during measurement in association with determination of systolic and diastolic pressure. Publication U.S. Pat. No. 4,117,835, for example, discloses a method of monitoring the change in the AC signal derivative. However, in clinical measurements said methods have not been found to affect the accuracy.

A tonometric method, originally designed for ocular pressure measurement, has also been applied to blood pressure measurement. In the methods according to publication U.S. Pat. No. 5,033,471, the radial artery extending near a radius of the wrist is pressed. Since the surface resting against the sensor is even, intravenous pressure can be read at the middle sensor element. The method thus involves a direct non-invasive measurement. In principle the measurement is ideal and practical, but the skin causes a problem since it does not provide an ideal membrane between the sensor and the blood vessel. This is why calibration is required in tonometric methods, as described in e.g. publication U.S. Pat. No. 5,279,303.

SUMMARY OF THE INVENTION

It is an object of the present invention to provide a new kind of method and arrangement for blood pressure measurement, avoiding the problems of known solutions.

The object is achieved by a method according to the invention, characterized by transferring the measured value of the variable pressure acting on the measuring point at the compression point to such an interpreting unit to which is also applied the pressure pulse generated by the heart and measured by a sensor at said second point for determining the effect of the variable acting pressure, and by determining diastolic pressure in the interpreting unit on the basis of such an acting pressure which is measured by a measuring element and which is the acting pressure when the interpreting unit detects a sufficiently long-standing change in a pressure pulse signal measured by said sensor.

The object is achieved by a method according to the invention, characterized by transferring the measured value of the variable pressure acting on the measuring point at the compression point to such an interpreting unit to which is also applied the pressure pulse generated by the heart and measured by a sensor at said second point for determining the effect of the variable acting pressure, and by determining systolic pressure in the interpreting unit on the basis of such an acting pressure which is the acting pressure when the interpreting unit detects a sufficiently long-standing change in a pressure pulse signal measured by said sensor.

The measurement arrangement of the invention is characterized by using as the sensor for measuring the effect of the variable acting pressure at the second point said sensor which measures the pressure pulse generated by heartbeat and which is coupled to such an interpreting unit to which is also coupled a measured signal indicating the measured value of the acting pressure, and that the interpreting unit is arranged to determine diastolic pressure on the basis of such an acting pressure which is the pressure acting when the interpreting unit detects a change characteristic of diastolic pressure in a pressure pulse signal measured by the sensor which measures the artery.

The measurement arrangement of the invention is characterized by using as the sensor for measuring the effect of the variable acting pressure at the second point said sensor which measures the pressure pulse generated by heartbeat and which is coupled to such an interpreting unit to which is also coupled a measured signal indicating the measured value of the acting pressure, and that the interpreting unit is arranged to determine systolic pressure on the basis of such an acting pressure which is the pressure acting when the interpreting unit detects a change characteristic of systolic pressure in a pressure pulse signal measured by the sensor which measures the artery.

The method and measurement arrangement of the invention are based on the idea of using a sensor, which measures the pressure pulse and transfers its measurement data to the interpreting unit, to indicate from the measured acting pressure signal the points conforming with diastolic and/or systolic pressure.

The solution of the invention provides a plurality of advantages. The invention provides an extremely good measurement accuracy, allowing systolic and/or diastolic pressure to be determined extremely accurately, since their detection is based on a separate measurement of the pressure pulse, which is used to indicate the values of said systolic and/or diastolic pressures.

BRIEF DESCRIPTION OF THE DRAWINGS

In the following the invention will be described in greater detail with reference to the attached drawings, in which.

DETAILED DESCRIPTION OF THE INVENTION

Figure 1:
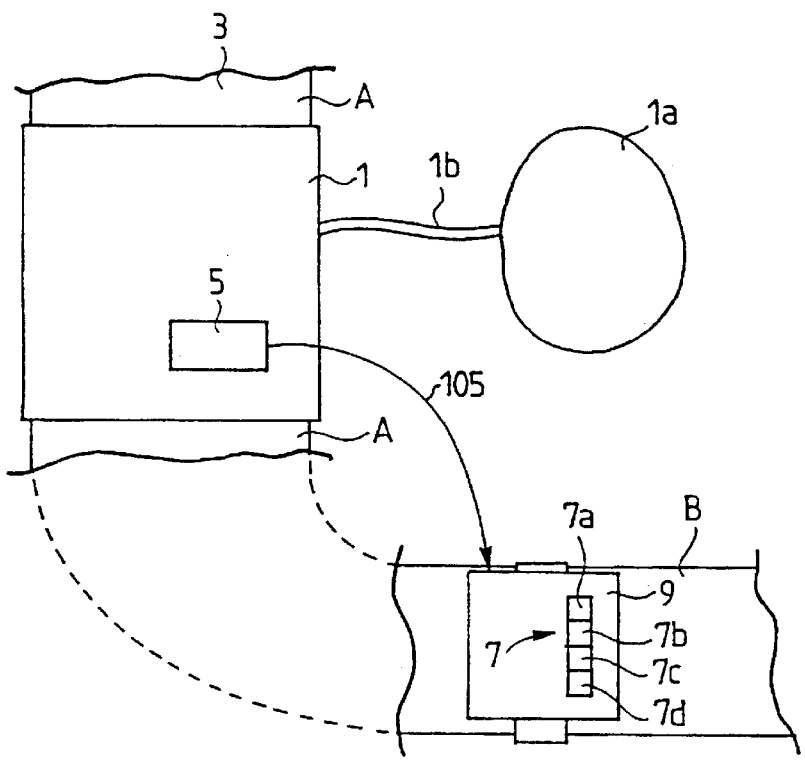
FIG. 1 shows a first embodiment of the measurement arrangement.

The invention relates to a method and an arrangement for blood pressure measurement. The measurement arrangement will be described first. The measurement arrangement comprises a cuff-like or other type of pressure generator 1, for applying pressure to a measuring point 3, such as a person's extremity 3 or the like, at a compression point A. The cuff-type pressure generator 1 obtains its pressure from a pressure source 1a, comprised by the arrangement, via a pressure line 1b. The pressure source 1a can be e.g. a pump.

The pressure serves to occlude the artery in the extremity 3 upon pressing and to open the artery when the pressure is released. The arrangement further comprises an element 5 for measuring the magnitude of the pressure generated by the pressure generator 1 for applying the pressure to the compression point A. The measuring element 5 can be e.g. a Si pressure sensor or other DC pressure sensor. The arrangement further comprises a sensor 7 for simultaneously measuring the effect of the variable acting pressure on an artery at a second point B. The sensor 7 can be e.g. a PVDF sensor (PolyVinylDiFluoride) or an EMF sensor (Electro Mechanical Film). Said second point B is a point which is farther away from the heart, i.e. closer to the end point of peripheral circulation than the compression point A, to which the pressure is applied. The measuring point B is thus at the distal, i.e. peripheral, side of the circulation. The measurement arrangement further comprises an interpreting means 9 for determining systolic and/or diastolic pressure. The interpreting unit 9 does not necessarily have to be a separate unit, but can also be integrated with the other means.

Figure 3:
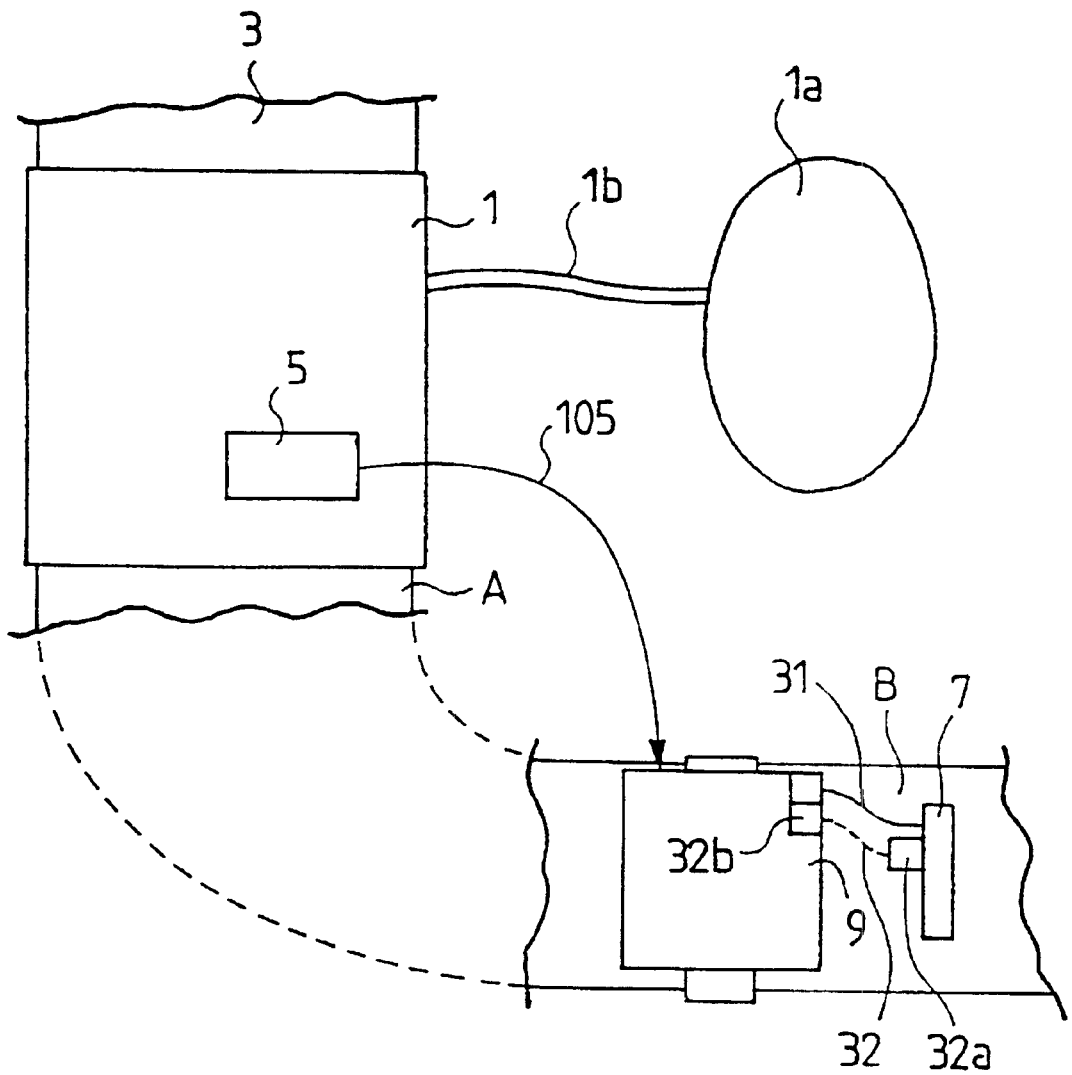
FIG. 3 shows a third embodiment of the measurement arrangement.

Said sensor 7 measures at the second point B the pressure pulse caused by heartbeat and is preferably separate from the pressure generator. The sensor 7 is coupled to said interpreting unit 9, to which a measuring signal, which is obtained from the measuring element 5 and depicts the measurement value of the acting pressure, is also coupled. In FIGS. 1 and 3, arrow 105 shows the transfer of the acting pressure from the measuring element 5 to the interpreting unit 9 in a simplified manner. The pressure pulse is preferably measured by a sensor 7 which, at least from the point of view of the technical operation of the measurement, is separate from the pressure generator, i.e. the sensor 7 measures the pressure pulse, i.e. the effect of the acting pressure, independently, not from the same signal source as the measuring element 5 measuring the acting pressure.

In some embodiments the sensor 7 can be in connection with the pressure generator or parts in connection therewith by e.g. a rod or conductor or otherwise, but in this case the pressure generator must be of a type which does not interfere with the operation of the sensor.

According to FIGS. 1 and 3, in the measurement arrangement said interpreting unit 9 is preferably a wristband-type unit 9, which in FIG. 1 comprises a pressure pulse sensor 7 for measuring the artery. This makes the measurement arrangement integrated and compact. In this preferred embodiment the method is such that the measured signal comprising the measured value of the acting pressure is transferred to said wristband type of interpreting unit, said interpreting unit 9 also being arranged to measure the pressure pulse by means of said pressure pulse measuring sensor 7 comprised by (FIG. 1) the interpreting unit 9 or being otherwise in connection (FIG. 3) therewith.

Figure 2:
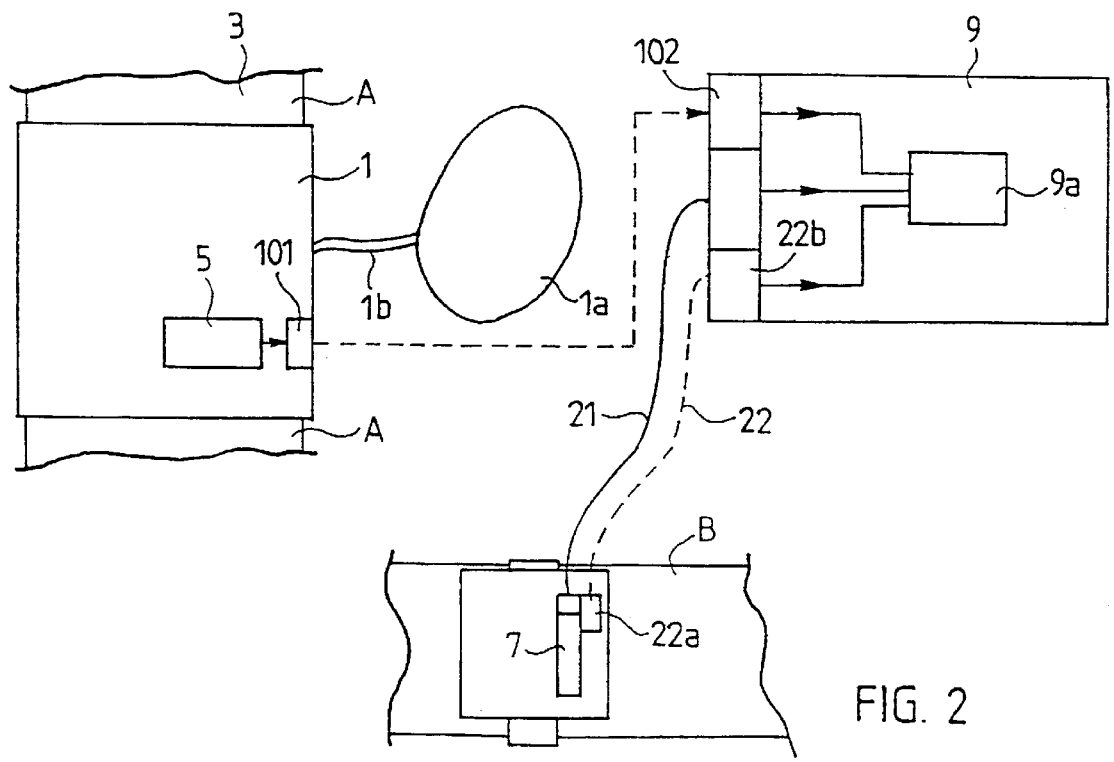
FIG. 2 shows a second embodiment of the measurement arrangement.

Referring to FIG. 2, an alternative solution can involve a separate interpreting unit, implemented by e.g. a microcomputer/measuring device or the like, the sensor 7 measuring the arterial pressure pulse signal being in a wired connection 21 or in a wireless connection 22 with said interpreting unit 9. The wired connection 21 could be e.g. a cable 21 between the sensor 7 and the interpreting unit 9, i.e. a computer/measuring device provided with e.g. a measuring card. In FIG. 2, a dashed line 22 denotes a wireless connection between the arterial pressure pulse sensor 7 and the interpreting unit 9. The wireless connection 22 is preferably implemented by a magnetic inductive coupling 22a, 22b, comprising a transmitter element 22a controlled by the sensor 7 and comprising a coil, and a receiver element 22b disposed in the interpreting unit 9 and comprising a second coil.

A combination of the previous versions, i.e. a third embodiment in accordance with FIG. 3, is also feasible, i.e. the interpreting unit 9 can be a wristband-type unit, but in FIG. 3 the pressure pulse sensor 7 measuring the artery is not integrated with the interpreting unit 9, but is in a wired connection 31 or a wireless connection 32 with the interpreting unit 9. The connections 31, 32 can be implemented in the same way as was presented for the version of FIG. 2, i.e. by a cable 31 or as a magnetic inductive coupling 32. Reference numerals 32a, 32b denote the transmitter element 32a and receiver element 32b of the wireless telemetric magnetic inductive coupling.

In a preferred embodiment of the invention the pressure pulse sensor 7 is a multichannel sensor, most preferably a line sensor, i.e. an array sensor. In this case the pressure pulse is measured as a multichannel measurement. The different channels 7a to 7d of the multichannel line sensor 7 are shown in FIG. 1 in a simplified form. This provides a more reliable measurement result than with a mere single-channel sensor. The different channels 7a to 7d of the multichannel sensor 7 are shown in FIG. 1 in a simplified manner.

In a preferred embodiment, the pressure pulse is measured in the radial artery area, where the arterial pressure pulse is easily detectable, and which is an easy point from the point of view of the subject of the measurement.

Referring to FIGS. 1 to 6, in the measurement arrangement said interpreting unit 9 is arranged to determine diastolic pressure PDIAS and systolic pressure PSYS on the basis of an acting pressure which is the acting pressure when a change characteristic of diastolic pressure PDIAS and a change characteristic of systolic pressure PSYS are detected by the interpreting unit 9, more exactly by the interpreting element 9a comprised by it, in the pressure pulse signal measured by the sensor 7 measuring the artery (the arterial pressure pulse).

A measurement arrangement of the type described above allows the implementation of a method for blood pressure measurement, the method comprising applying a variable compressive acting pressure to a measuring point, such as a person's extremity 3 or the like measuring point 3 at a compression point A, and at the same time the effect of the variable acting pressure on the artery is measured at a second point B. The method is characterized by transferring the measured value of the variable pressure acting on the measuring point at the compression point A from the measuring element 5 to an interpreting unit 9 to which is also applied the magnitude, preferably amplitude, of the pressure pulse generated by the heart and measured by the sensor 7 at said second point B. As was stated above, the sensor 7 is preferably separate from the pressure generator 1, i.e. the cuff 1, whereby in the preferred embodiment the pressure pulse is measured with the sensor 7 at a point which is at least as far away from the pressure generator 1 as the point to which the reach area of the pressure oscillation of the pressure generator extends. In this case the pressure variation in the cuff 1 does not interfere with the measurement of the pressure pulse. The method is characterized by determining diastolic pressure PDIAS in the interpreting unit 9 on the basis of an acting pressure which is the acting pressure when the interpreting unit 9 detects a sufficiently long-lasting change in the magnitude, preferably amplitude, of the pressure pulse signal measured by said sensor 7. As regards systolic pressure PSYS, the method is characterized in that systolic pressure is measured in the interpreting unit 9 on the basis of a second acting pressure which is the acting pressure when the interpreting unit 9 detects a sufficiently long-lasting change of a second type in the magnitude, for example amplitude, of the pressure pulse signal measured by said sensor 7.

In the embodiments disclosed in the present application the pressure pulse is most preferably measured as an amplitude measurement, and naturally monitoring the magnitude of the pressure pulse is also based on monitoring amplitude values. However, instead of amplitude, the sensor 7 can measure pressure pulse frequency or phase, which also serve to indicate the magnitude of the pressure pulse, and hence, amplitude. The measurement may also involve amplitude measurement, amplitude data being converted into frequency or phase data. Thus the present invention is not only restricted to direct amplitude measurement and comparison by means of amplitude.

In the method, the measurement of the variable acting pressure with the measuring element 5 and the measurement of the pressure pulse, e.g. its amplitude, with the sensor 7 are used to form the magnitude of the pressure pulse, such as amplitude data, as a function of the acting pressure. Systolic pressure PSYS and/or diastolic pressure PDIAS is determined in the interpreting unit 9 on the basis of said function. The sensor 7, which is preferably physically completely separate from the pressure generator 1, i.e. the cuff 1, consequently operates as an indicator of the interpreting unit 9, indicating to the interpreting unit 9 whether the magnitude of the acting pressure of the cuff 1 indicates the magnitude of diastolic pressure PDIAS or the magnitude of systolic pressure PSYS.

Figure 4:
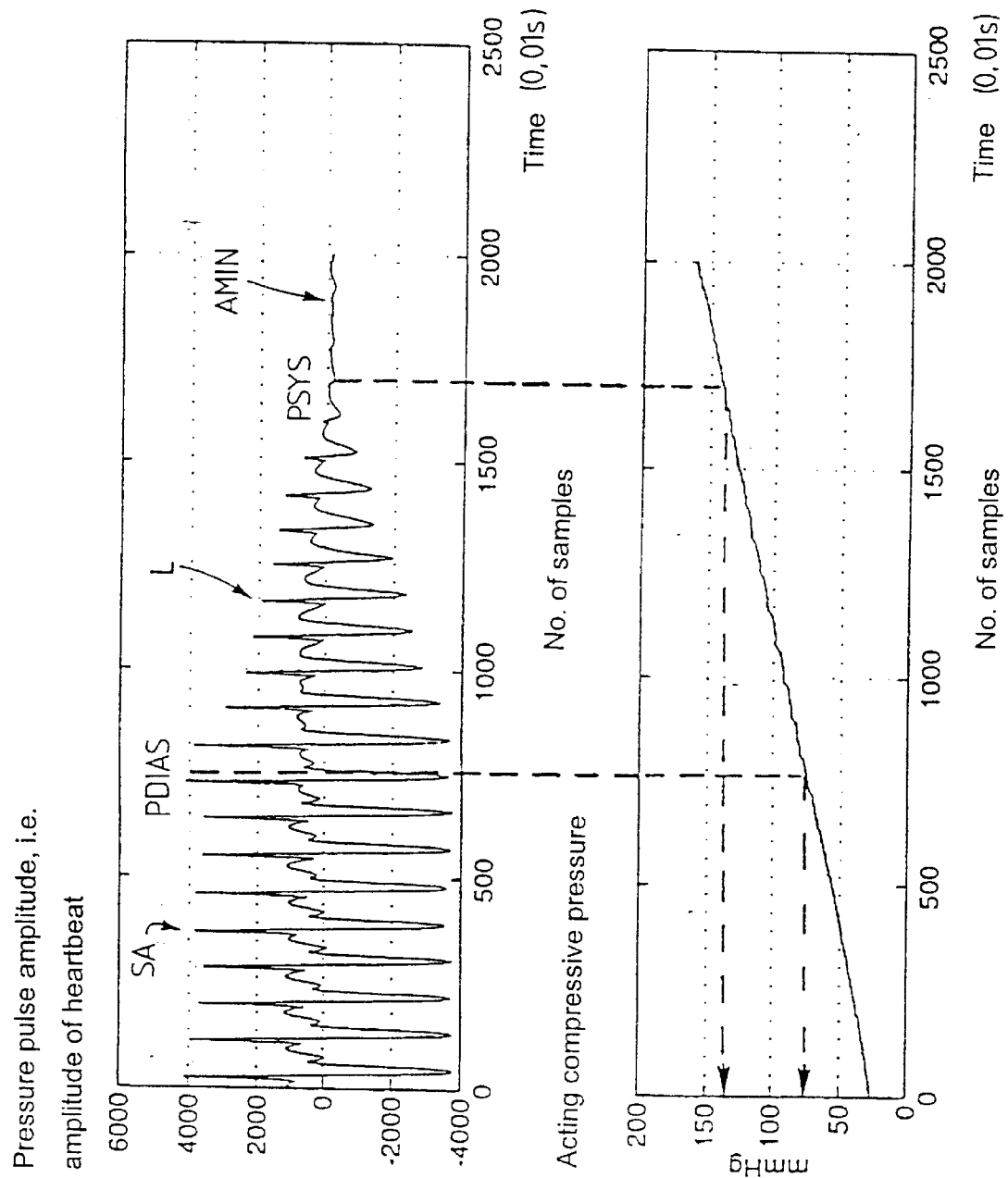
FIG. 4 shows blood pressure measurement during a rising acting pressure.

In a preferred embodiment, unlike in methods and arrangements employing the conventional determination of the acting pressure during falling acting pressure, the method employs rising acting pressure in accordance with FIG. 4. In this case the blood pressure measurement is carried out when the acting pressure is raised. Measurement during rising pressure is more convenient to the subject, since the acting pressure does not have to be raised too high. This situation involves determination of diastolic pressure PDIAS in a measurement during rising acting pressure on the basis of an acting pressure equal to the pressure acting when the interpreting unit 9 detects during measurement of the pressure pulse, e.g. its amplitude, by the sensor 7, that the magnitude of the pressure pulse, e.g. its amplitude, starts to fall. Similarly, systolic pressure PSYS is determined on the basis of an acting pressure equal to the pressure acting when the interpreting unit 9, 9a detects during measurement of the pressure pulse, e.g. its amplitude, by the sensor 7, that the magnitude of the pressure pulse, e.g. its amplitude, stops falling.

More specifically and still referring to FIG. 4, the method is preferably such that in a measurement made during rising acting pressure, diastolic pressure PDIAS is determined on the basis of an acting pressure equal to the pressure acting when it is detected during measurement of the pressure pulse, e.g. its amplitude, that an essentially constant value of the pressure pulse, e.g. its amplitude, starts to fall substantially linearly. In FIG. 4 said constant amplitude range is denoted by SA, and the linear range is denoted by L. Similarly, systolic pressure PSYS is determined on the basis of an acting pressure equal to the pressure acting when it is detected during measurement of the pressure pulse, e.g. its amplitude, that the amplitude of the substantially directly linearly falling pressure pulse stops falling and reaches its minimum value AMIN, which substantially corresponds to zero. It is easier to detect such points by the sensor 7 and the interpreting unit 9, and a more accurate measurement is also achieved.

Figure 5:
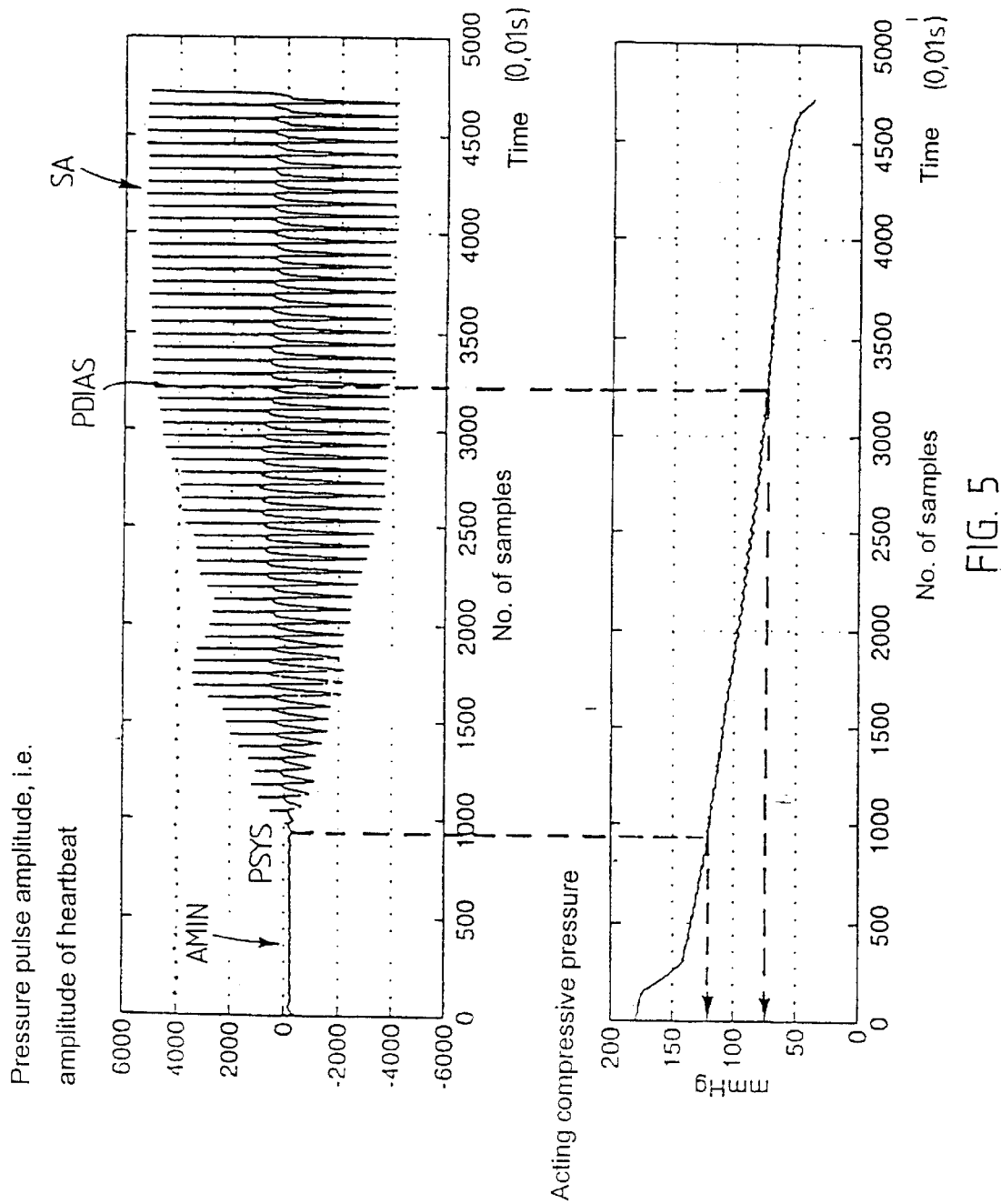
FIG. 5 shows blood pressure measurement during a falling acting pressure.

An alternative is a second preferred embodiment in accordance with FIG. 5, in which said variable acting pressure is a falling acting pressure, and blood pressure is measured as the acting pressure is lowered. The method is most preferably such that systolic pressure PSYS is determined in a measurement during falling acting pressure on the basis of an acting pressure equal to the pressure which is acting when the interpreting unit 9 detects in a signal measured by the sensor 7 in a pressure pulse measurement that the amplitude of the pressure pulse starts to increase. Similarly, diastolic pressure PDIAS is determined on the basis of an acting pressure equal to the pressure acting when the interpreting unit 9 detects in a signal measured by the sensor 7 in a pressure pulse measurement that the amplitude of the pressure pulse stops increasing.

More specifically and still referring to FIG. 5, the method is preferably such that in a measurement made during falling acting pressure, systolic pressure PSYS is determined on the basis of an acting pressure equal to the pressure acting when the interpreting unit 9 detects during measurement of the pressure pulse by the sensor 7 that the amplitude of the pressure pulse starts to increase from its minimum amplitude value AMIN which substantially corresponds to zero. Similarly, diastolic pressure PDIAS is determined on the basis of an acting pressure equal to the pressure acting when the interpreting unit 9 detects during a pressure pulse measurement made by the sensor 7 that the amplitude of the pressure pulse stops increasing and reaches its constant value, such as the amplitude value SA having constant amplitude.

It is easier to detect such precisely shaped points and ranges by the interpreting unit 9, and a more accurate measurement is also achieved.

Figure 6:
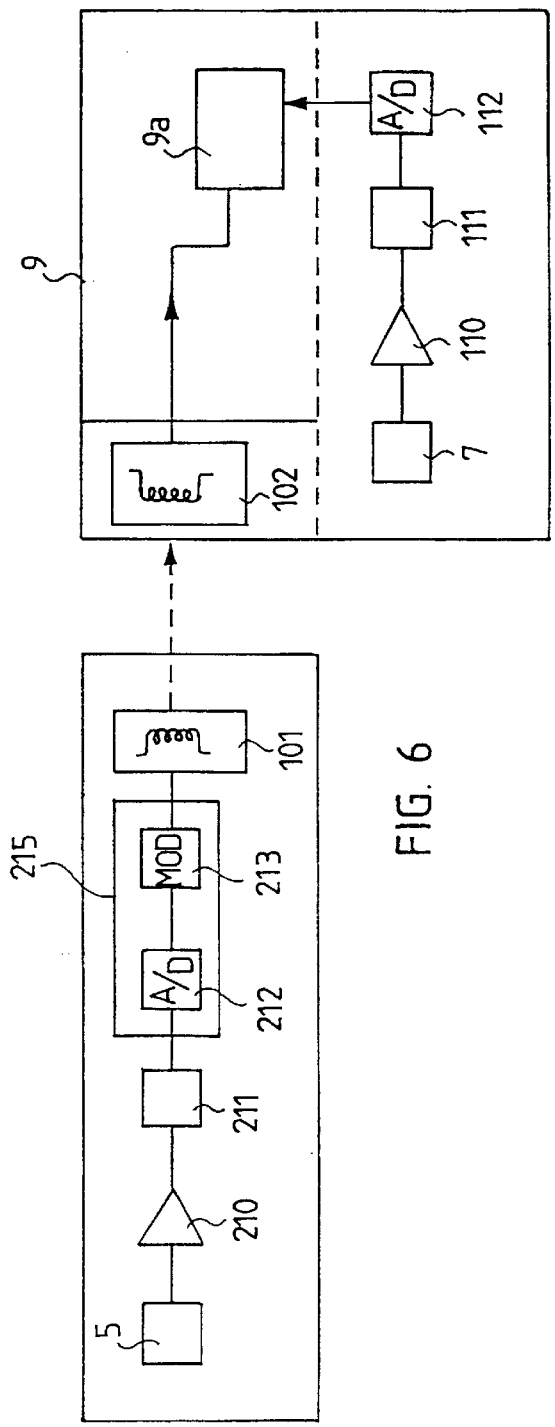
FIG. 6 shows an embodiment for transferring measurement data on the acting pressure and on the pressure pulse to the interpreting unit.

FIG. 6 shows an embodiment for transferring measurement data measured by the acting pressure measuring element 5 in connection with the pressure generator to the interpreting unit 9. FIG. 6 also shows an embodiment for processing the signal measured by the pressure pulse sensor 7 and for transferring it to the interpreting unit 9.

Referring to FIG. 6, a preferred embodiment of the invention involves a measurement arrangement comprising a wireless telemetric magnetic inductive coupling 101, 102 for transferring the measured acting pressure measuring signal from the measuring element 5 to the interpreting unit 9. Said coupling comprises a transmitter element 101, which obtains input data from the acting pressure measuring element 5, and a receiver element 102 in the interpreting unit 9. The transmitter element 101 comprises a coil 101a, to which the signal measured by the measuring element 5 is applied. The receiver element 102 comprises a second coil 102a. In the method the acting pressure measurement value is transferred to the interpreting unit 9 as a wireless telemetric transfer by means of the magnetic inductive coupling 101, 102 between the coils 101a, 102a. The connection 105 for transferring the signal measured by the acting pressure measuring element 5 to the interpreting unit 9, shown in FIGS. 1 and 3 in a simplified manner by arrow 105, can be a wired connection or wireless, as the transfer implemented by the inductive coupling by the components 101, 102 in FIGS. 2 and 6.

In accordance with FIG. 6, in a preferred embodiment the measurement arrangement comprises an amplifier 110 and a filter 111 for amplifying and filtering the pressure pulse signal measured by the sensor 7, and an A/D converter 112 for performing A/D conversion after filtering. The amplifier 110 can be e.g. a voltage or charging amplifier. The filter 111, in turn, is preferably a band-pass filter whose passband is e.g. within the range 1 to 10 Hz.

Figure 7:
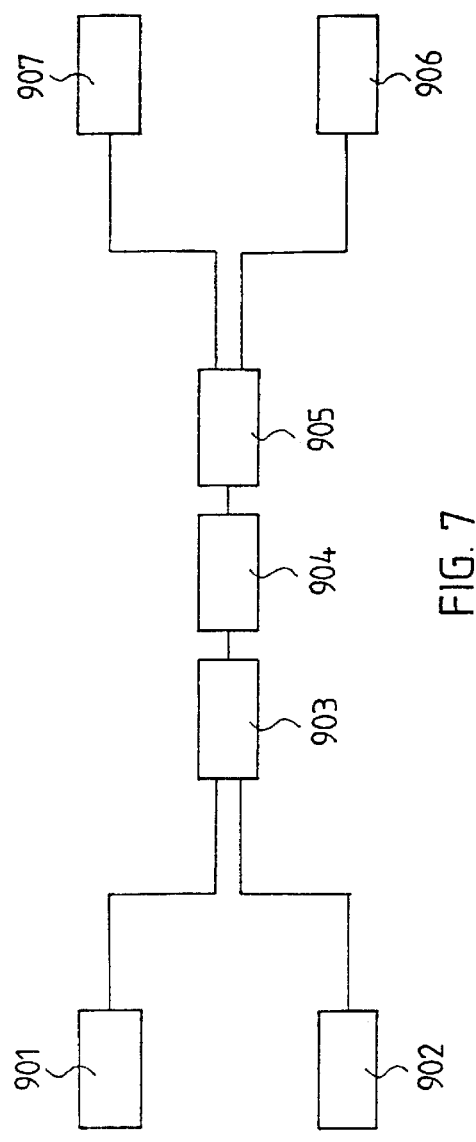
FIG. 7 shows the inner structure of the interpreting element comprised by the interpreting unit.

The method is preferably such that the pressure pulse signal measured by the sensor 7 is amplified by the amplifier 110 and filtered by the filter 111, and then A/D converted by the converter 112. The amplification and filtering serve to eliminate interference and distortion, resulting in a sufficiently strong signal. The A/D conversion, in turn, converts the measured signal into a form which the interpreting unit 9 is able to interpret and process. FIGS. 2, 5 and 7 show the interpreting element 9a, e.g. a microprocessor, comprised by the interpreting unit 9. The versions shown by the other figures also comprise a similar component.

In fact, FIG. 7 shows the inner structure of the interpreting element 9a comprised by the interpreting unit 9. In FIG. 7, the interpreting element 9a comprises a part 901 for identifying the active pressure measurement signal, a part 902 for identifying the pressure pulse signal, a signal check part 903 connected to parts 901 and 902, a straight line fitting part 904 connected to part 903 and a SYS/DIAS determining part 905 connected to part 904. The SYS/DIAS determining part 905 determines the values of systolic and/or diastolic pressure according to what the straight line fitting algorithm (least squares principle) in the straight line fitting part 903 indicates on the basis of the received pressure measuring signal and pressure pulse signal. The straight line fitting algorithm serves to convert a discrete measurement into a form with continuous values.

In a preferred embodiment the interpreting unit 9a comprises, or at least has a connection to, a memory 906 and a display 907. The memory 906 and the display 907 can be external parts with respect to the interpreting element 9a, belonging, however, to the interpreting unit 9.

In the most practical solution of the measurement arrangement of a preferred embodiment both diastolic and systolic pressure are determined. In this case both diastolic and systolic pressure are determined by common means 5, 7, 9, 901 to 907. This makes the method and the measurement arrangement more usable.

In a preferred embodiment of the invention the measurement arrangement comprises an amplifier 210 and a filter 211 for filtering the acting pressure measuring signal obtained from the measuring element 5 to filter off an oscillating AC portion caused by the pulse. The measuring element 5 carries out a pressure/voltage conversion, for example, and in this case the amplifier 210 is a voltage amplifier. The filter 211, in turn, is a low-pass filter with an upper limit frequency of e.g. 1 to 5 Hz.

In a preferred embodiment, the arrangement further comprises an A/D converter 212 for AND conversion of the filtered acting pressure signal. If an inductive coupling 101, 102 is used for transferring the signal measured by the acting pressure measuring element 5 to the interpreting unit 9, then the arrangement further comprises a modulator 213 or another signal modulator unit 213 for modulating the AND converted signal e.g. to a frequency modulated signal or to another signal which can be applied to the transmitter unit 101 comprised by the inductive coupling. The signal modulator unit 213 can be e.g. a pulse width modulator or a frequency modulator. Together the blocks 212 and 213 form a signal modulator 215 which serves to modulate the signal into a transferable form for the transmitter element 101. It should be observed that the connection 101–102 could alternatively be optic.

Said units 210 to 213 and 101 are most preferably part of the same entity as are the measuring unit 5 and the pressure generator 1. The method thus preferably comprises a step of filtering the measured acting pressure signal by the filter 211 to filter off an oscillating AC portion caused by heartbeat. In said preferred embodiment, the determination of systolic pressure PSYS and diastolic pressure PDIAS employ the filtered acting pressure of the measured signal, obtained by filtration, and the information contained therein is transferred to the interpreting unit 9. The measured acting pressure signal is preferably amplified by the amplifier 210 before the measured acting pressure signal is filtered, and A/D conversion by the A/D converter 212 is carried out after filtration. In other words, the solution of the preferred embodiment employs in determining systolic pressure PSYS and diastolic pressure PDIAS an acting pressure signal which has been subjected to A/D conversion and from which the interpreting unit 9 calculates the blood pressure values from the measured signal originating from the measuring element 5 by using as indicator the signal of the sensor 7 measuring the artery. Thus the portion obtained from the filtration of the acting pressure measured by the measuring element 5 in connection to the pressure generator 1, i.e. the cuff 1, is the acting pressure from which the arterial pressure pulse measuring sensor 7 "indicates" the blood pressure values. Filtering off the AC portion, i.e. the use of a filtered acting pressure, results in an acting pressure measurement result having less interference, since the effect of heartbeat, which causes AC oscillation in the acting pressure, on the cuff can be eliminated by filtration.

The magnetic inductive coupling described above in different contexts, is based on applying a current with varying magnitude to the coil of the transmitter element, the coil generating a magnetic field with varying magnitude, the field being received by a second coil, i.e. by the coil of the receiver element. A magnetic inductive coupling is useful in small portable devices owing to its low power consumption. An inductive coupling is particularly useful in wristband-type versions according to FIGS. 1 and 3.

The preferred embodiments of the invention described above and the other features of the method and measurement arrangement presented in greater detail highlight the advantages of the basic invention.

Although the invention is described herein with reference to the examples in accordance with the accompanying drawings, it will be appreciated that the invention is not to be so limited, but can be modified in a variety of ways within the scope of the inventive idea disclosed in the appended claims.

What is claimed is:

1. A method for blood pressure measurement, comprising applying a variable compressive acting pressure to a measuring point at a compression point by a pressure generator, and at the same time using a sensor to measure an arterial pressure pulse under the effect of the variable acting pressure on the artery at a second point, the second point being located farther away from the heart than the compression point to which the acting pressure is applied, characterized by providing a signal representing the measured value of the variable pressure acting on the measuring point at the compression point to an interpreting unit, sending a pressure pulse signal representing the measured arterial pressure pulse from the sensor to the interpreting unit, and determining diastolic pressure in the interpreting unit on the basis of the variable acting pressure when the interpreting unit detects a change in trend in a characteristic indicative of the magnitude of the pressure pulse in the pressure pulse signal from said sensor.

2. A method as claimed in claim 1, characterized in that pressure pulse measurement data is generated as a function of the acting pressure on the basis of the measurement of the variable acting pressure employed in the method and the measurement of the pressure pulse, systolic and/or diastolic pressure being determined in the interpreting unit on the basis of said function.

3. A method as claimed in claim 1, characterized in that said variable acting pressure is a falling acting pressure, and that blood pressure is measured when the acting pressure is lowered.

4. A method as claimed in claim 3, characterized in that in the measurement performed during falling acting pressure, systolic pressure is determined on the basis of an acting pressure equal to the pressure acting when it is detected in pressure pulse measurement that the magnitude of the pressure pulse starts to increase.

5. A method as claimed in claim 1, characterized in that the pressure pulse is measured in the area of the radial artery.

6. A method as claimed in claim 1, characterized in that the pressure pulse is measured as a multichannel measurement.

7. A method as claimed in claim 6, characterized in that the pressure pulse is measured by a line sensor.

8. A method as claimed in claim 1, characterized by transferring the measured signal containing the measured value of the acting pressure to said wristband type of interpreting unit, which is also arranged to measure the pressure pulse by means of said pressure pulse measuring sensor comprised by it or otherwise being in connection thereto.

9. A method as claimed in claim 1, characterized by transferring the measured value of the acting pressure to the interpreting unit as a wireless telemetric transfer by means of a magnetic inductive coupling.

10. A method as claimed in claim 1, characterized in that the pressure pulse signal measured by the sensor is amplified and filtered, and then subjected to A/D conversion.

11. A method as claimed in claim 1, characterized in that the measured acting pressure signal is filtered to filter off the oscillating AC portion caused by heartbeat to generate a measured filtered acting pressure signal.

12. A method as claimed in claim 11, characterized in that the filtered measured acting pressure signal is used in the determination of systolic and/or diastolic pressure.

13. A method as claimed in claim 11, characterized in that before the measured acting pressure signal is filtered, it is amplified, and after filtration subjected to conversion to modify it to a transferable form, and that said signal conversion includes A/D conversion followed by modulation.

14. A method as claimed in claim 1, characterized by measuring both diastolic and systolic pressure, and by said change in trend in a characteristic indicative of the magnitude of the pressure pulse, observed by the pressure pulse meaning sensor, being different for diastolic and for systolic pressure.

15. A method as claimed in claim 1, characterized in that the pressure pulse is measured with the sensor from a point which is at least as far away from the pressure generator as the point to which the reach area of the pressure oscillation of the pressure generator extends.

16. A method as claimed in claim 15, characterized in that an inflatable cuff is used as the pressure generator.

17. A method as claimed in claim 1, characterized in that the pressure pulse is measured with a sensor which is separate from the pressure generator at least from the point of view of the technical operation of the measurement.

18. A method as claimed in claim 1, characterized in that the pressure pulse is measured with a sensor which is physically detached from the pressure generator.

19. A method as claimed in claim 1, characterized in that the sensor measures the amplitude, frequency or phase of the pressure pulse.

20. A method for blood pressure measurement, comprising applying a variable compressive acting pressure to a measuring point, at a compression point by a pressure generator, and at the same time using a sensor to measure an arterial pressure pulse under the effect of the variable acting pressure on the artery at a second point, the second point located farther away from the heart than the compression point to which the acting pressure is applied, characterized by providing a signal representing the measured value of the variable pressure acting on the measuring point at the compression point to an interpreting unit, sending a pressure pulse signal representing the measured arterial pressure pulse from the sensor to the interpreting unit, and determining systolic pressure in the interpreting unit on the basis of the variable pressure when the interpreting unit detects a change in trend in a characteristic indicative of the magnitude of the pressure pulse in the pressure pulse signal from said sensor.

21. A method for blood pressure measurement, comprising:

applying a variable compressive acting pressure to a measuring point at a compression point by a pressure generator, wherein said variable acting pressure is a rising acting pressure, and at the same time using a sensor to measure an arterial pressure pulse under the effect of the variable acting pressure on the artery at a second point, the second point being located farther away from the heart than the compression point to which the acting pressure is applied, providing a signal representing the measured value of the variable pressure acting on the measuring point at the compression point to an interpreting unit, sending a pressure pulse signal representing the measured arterial pressure pulse from the sensor to the interpreting unit, and determining diastolic pressure in the interpreting unit on the basis of an acting pressure equal to the pressure acting when it is detected in pressure pulse measurement that the magnitude of the pressure pulse signal from said sensor starts to decrease.

22. A method as claimed in claim 21, characterized in that in the measurement performed during rising acting pressure, diastolic pressure is determined on the basis of an acting pressure equal to the pressure acting when it is detected in pressure pulse measurement that the substantially constant value of the pressure pulse starts to decrease substantially linearly.

23. A method for blood pressure measurement, comprising:
   applying a variable compressive acting pressure to a measuring point at a compression point by a pressure generator, wherein said variable acting pressure is a rising acting pressure, and at the same time using a sensor to measure an arterial pressure pulse under the effect of the variable acting pressure on the artery at a second point, the second point located farther away from the heart than the compression point to which the acting pressure is applied,
   providing a signal representing the measured value of the variable pressure acting on the measuring point at the compression point to an interpreting unit,
   sending a pressure pulse signal representing the measured arterial pressure pulse from the sensor to the interpreting unit, and
   determining systolic pressure in the interpreting unit on the basis of an acting pressure equal to the pressure acting when it is detected in pressure pulse measurement that the magnitude of the pressure pulse signal from said sensor stops decreasing.

24. A method as claimed in claim 23, characterized in that systolic pressure is determined on the basis of an acting pressure equal to the pressure acting when it is detected in pressure pulse measurement that the magnitude of the pressure pulse, which decreases substantially directly linearly, stops decreasing and reaches its minimum value, which substantially corresponds to zero.

25. A method for blood pressure measurement, comprising:
   applying a variable compressive acting pressure to a measuring point at a compression point by a pressure generator, wherein said variable acting pressure is a falling acting pressure, and at the same time using a sensor to measure an arterial pressure pulse under the effect of the variable acting pressure on the artery at a second point, the second point being located farther away from the heart than the compression point to which the acting pressure is applied,
   providing a signal representing the measured value of the variable pressure acting on the measuring point at the compression point to an interpreting unit,
   sending a pressure pulse signal representing the measured arterial pressure pulse from the sensor to the interpreting unit, and
   determining diastolic pressure in the interpreting unit on the basis of an acting pressure equal to the pressure acting when it is detected in pressure pulse measurement that the magnitude of the pressure pulse signal from said sensor stops increasing.

26. A method as claimed in claim 25, characterized in that diastolic pressure is determined on the basis of an acting pressure equal to the pressure acting when it is detected in pressure pulse measurement that the magnitude of the pressure pulse stops increasing and reaches a constant value.

27. A method for blood pressure measurement, comprising:
   applying a variable compressive acting pressure to a measuring point at a compression point by a pressure generator, wherein said variable acting pressure is a falling acting pressure, and at the same time using a sensor to measure an arterial pressure pulse under the effect of the variable acting pressure on the artery at a second point, the second point located farther away from the heart than the compression point to which the acting pressure is applied,
   providing a signal representing the measured value of the variable pressure acting on the measuring point at the compression point to an interpreting unit,
   sending a pressure pulse signal representing the measured arterial pressure pulse from the sensor to the interpreting unit, and
   determining systolic pressure in the interpreting unit on the basis of an acting pressure equal to the pressure acting when it is detected in pressure pulse measurement that the magnitude of the pressure pulse signal from said sensor starts to increase from its minimum value which substantially corresponds to zero.

28. An arrangement for blood pressure measurement, comprising a pressure generator for applying a compressive acting pressure to a measuring point, an acting pressure measuring element, an interpreting unit arranged to determine diastolic pressure, a sensor for simultaneous measurement of the effect of the variable acting pressure on an artery at a second point and for generating a pressure pulse signal representing a measured arterial pressure pulse, said second point being farther away from the heart, i.e, closer to the end point of peripheral circulation, than the compression point to which the acting pressure is applied,
   said sensor which measures the pressure pulse generated by heartbeat being coupled to said interpreting unit to which is also coupled the acting pressure measuring element, and that the interpreting unit is arranged to determine diastolic pressure on the basis of an acting pressure which is the pressure acting when the interpreting unit detects a change characteristic of diastolic pressure in a pressure pulse signal measured by the sensor which measures the artery.

29. An arrangement as claimed in claim 28, characterized in that said interpreting unit is a wristband or other type of unit comprising said pressure pulse sensor measuring the artery.

30. An arrangement as claimed in claim 28, characterized in that said interpreting unit is a wristband or other type of unit which is in a wireless connection or a wired connection to said pressure pulse sensor measuring the artery.

31. An arrangement as claimed in claim 28, characterized in that the pressure pulse sensor is a multichannel sensor.

32. An arrangement as claimed in claim 28, characterized in that for transferring the measured acting pressure value to the interpreting unit, the arrangement comprises a wireless transmitter which receives input data from the acting pressure measuring element and a wireless receiver element in the interpreting unit.

33. An arrangement as claimed in claim 32, characterized by comprising a signal modulator for modulating the filtered acting pressure signal into a form suitable for the transmitter element before the signal is coupled to the transmitter element.

34. An arrangement as claimed in claim 33, characterized in that the signal modulator comprises a signal modulator unit (213).

35. An arrangement as claimed in claim 34, characterized in that the signal modulator unit a modulator, such as a pulse width modulator, frequency modulator or other modulator.

36. An arrangement as claimed in claim 34, characterized in that the signal modulator comprises and A/D converter which precedes the signal modulator unit and is used for A/D conversion of the measured filtered acting pressure signal.

37. An arrangement as claimed in claim 34, characterized in that diastolic and systolic pressure are determined by common means.

38. An arrangement claimed in claim 28, characterized in that for transferring the measured acting pressure value to the interpreting unit, the arrangement comprises a wireless telemetric magnetic inductive coupling comprising a wireless transmitter which receives input data from the acting pressure measuring element and a wireless receiver element in the interpreting unit.

39. An arrangement as claimed in claim 28, characterized by comprising an amplifier and a filter for amplifying and filtering the pressure pulse signal measured by the sensor, and an A/D converter for performing A/D conversion after the filtering.

40. An arrangement as claimed in claim 28, characterized by comprising a filter for filtering the measured acting pressure signal to filter off the oscillating AC portion for generating a measured filtered acting pressure signal.

41. An arrangement as claimed in claim 40, characterized in that before the filter for filtering off the AC portion, the arrangement comprises an amplifier for amplifying the measured acting pressure signal.

42. An arrangement as claimed in claim 40, characterized in that the filter which filters off the AC portion is a low-pass filter.

43. An arrangement as claimed in claim 42, characterized in that the upper limit frequency of the low-pass filter is between 1 and 5 Hz.

44. An arrangement as claimed in claim 28, characterized in that the measurement arrangement is arranged to determine both diastolic and systolic pressure.

45. An arrangement as claimed in claim 28, characterized in that an inflatable cuff is used as the pressure generator.

46. An arrangement as claimed in claim 28, characterized in that the pressure pulse is measured by the sensor at a point which is at least as far ways from the pressure generator as the point to which the reach area of the pressure oscillation of the pressure generator extends.

47. An arrangement as claimed in claim 28, characterized in that the pressure pulse is measured by the sensor which is separate from the pressure generator at least from the point of view of the technical operation of the measurement.

48. An arrangement as claimed in claim 28, characterized in that the pressure pulse is measured by a measuring sensor which is physically separate from the pressure generator.

49. An arrangement for blood pressure measurement, comprising a pressure generator for applying a compressive acting pressure to a measuring point, such as a person's extremity, the arrangement comprising an acting pressure measuring element, an interpreting unit arranged to determine systolic pressure, a sensor for simultaneous measurement of the effect of the variable acting pressure on an artery at a second point and for generating a pressure pulse signal representing a measured arterial pressure pulse, said second point being farther away from the heart than the compression point to which the acting pressure is applied, said sensor which measures the pressure pulse generated by heartbeat being coupled to said interpreting unit to which is also coupled the acting pressure measuring element, and that the interpreting unit is arranged to determine systolic pressure on the basis of an acting pressure which is the pressure acting when the interpreting unit detects a change characteristic of systolic pressure in a pressure pulse signal measured by the sensor which measures the artery.

50. An arrangement as claimed in claim 49, characterized in that the pressure pulse sensor is a line sensor.

51. An apparatus for determining systolic blood pressure comprising:

a pressure cuff for applying a variable pressure to a person's extremity;

a pressure generator connected to said pressure cuff, said pressure generator providing said variable pressure to said pressure cuff;

a measuring element for measuring the variable pressure provided by said pressure generator;

a sensor, said sensor being capable of detecting a pressure pulse in an artery in said extremity, said sensor capable of creating a pressure pulse signal; and an interpreting unit connected to said measuring element and said sensor for determining systolic pressure, said interpreting unit being capable of determining said systolic pressure on the basis of the variable pressure measured by the measuring element and a change in trend in a characteristic indicative of the magnitude of the pressure pulse in the pressure pulse signal received from said sensor.

52. An apparatus for determining diastolic blood pressure comprising:

a pressure cuff sized to fit around a person's extremity, said pressure cuff being capable of being inflated to variable pressures;

a pressure generator, said pressure generator being connected to said pressure cuff to create said variable pressure, a measuring element for measuring the variable pressure provided by said pressure generator;

a sensor, said sensor being capable of detecting a pressure pulse in an artery in said extremity, said sensor capable of creating a pressure pulse signal; and an interpreting unit, said interpreting unit being connected to said sensor and to said measuring element, said interpreting unit being capable of determining diastolic pressure on the basis of the variable pressure measured by the measuring element and a change in trend in a characteristic indicative of the magnitude of the pressure pulse in the pressure pulse signal received from said sensor.

* * * * *